US008748188B2

(12) United States Patent
Sampson et al.

(10) Patent No.: US 8,748,188 B2
(45) Date of Patent: Jun. 10, 2014

(54) METHOD OF PREPARING, STORING, TRANSPORTING AND TESTING CHLORINE DIOXIDE SOLUTIONS

(75) Inventors: Allison H. Sampson, Fair Oaks Ranch, TX (US); Richard L. Sampson, Fair Oaks Ranch, TX (US); George Dimotsis, Lansdale, PA (US)

(73) Assignees: Allison H. Sampson, Fair Oaks Ranch, TX (US); Richard L. Sampson, Fair Oaks Ranch, TX (US)

( * ) Notice: Subject to any disclaimer, the term of this patent is extended or adjusted under 35 U.S.C. 154(b) by 0 days.

(21) Appl. No.: 13/332,825

(22) Filed: Dec. 21, 2011

(65) Prior Publication Data

US 2012/0214248 A1    Aug. 23, 2012

Related U.S. Application Data

(60) Provisional application No. 61/457,094, filed on Dec. 23, 2010, provisional application No. 61/457,177, filed on Jan. 21, 2011.

(51) Int. Cl.
*G01N 1/28* (2006.01)
*G01N 31/00* (2006.01)
*G01N 1/00* (2006.01)

(52) U.S. Cl.
USPC ............................ 436/124; 436/176; 436/174

(58) Field of Classification Search
USPC ......................................... 436/124, 176, 174
See application file for complete search history.

(56) References Cited

U.S. PATENT DOCUMENTS

| | | | |
|---|---|---|---|
| 3,684,437 A | 8/1972 | Callerame et al. | |
| 3,828,097 A | 8/1974 | Callerame et al. | |
| 3,857,737 A | 12/1974 | Kemp et al. | |
| 4,504,442 A | 3/1985 | Rosenblatt et al. | |
| 4,681,739 A | 7/1987 | Rosenblatt et al. | |
| 4,880,711 A | 11/1989 | Luczak et al. | |
| 5,006,326 A * | 4/1991 | Mayurnik et al. | 423/477 |
| 5,008,096 A | 4/1991 | Ringo | |
| 5,078,908 A | 1/1992 | Ripley et al. | |
| 5,100,652 A | 3/1992 | Kross et al. | |
| 5,269,832 A * | 12/1993 | Meijer | 95/25 |
| 5,391,533 A | 2/1995 | Peterson et al. | |
| 5,435,984 A | 7/1995 | Daly et al. | |
| 5,573,743 A * | 11/1996 | Klatte et al. | 423/477 |
| 5,651,996 A | 7/1997 | Roozdar | |
| RE36,064 E | 1/1999 | Davidson et al. | |
| 6,063,425 A | 5/2000 | Kross et al. | |
| 6,077,495 A | 6/2000 | Speronello et al. | |
| 6,123,966 A | 9/2000 | Kross | |
| 6,171,485 B1 | 1/2001 | Kuke | |
| 6,200,557 B1 | 3/2001 | Ratcliff | |
| 6,238,643 B1 | 5/2001 | Thangaraj et al. | |
| 6,265,343 B1 | 7/2001 | Daly et al. | |
| 6,287,533 B1 | 9/2001 | Khan et al. | |
| 6,972,121 B2 * | 12/2005 | Pu et al. | 423/478 |
| 2001/0001655 A1 | 5/2001 | Kuke | |
| 2003/0092189 A1 * | 5/2003 | Johnson et al. | 436/125 |
| 2004/0071627 A1 | 4/2004 | DiMascio | |
| 2005/0095192 A1 | 5/2005 | DiMascio | |
| 2007/0253891 A1 * | 11/2007 | Sampson et al. | 423/477 |
| 2009/0142226 A1 * | 6/2009 | McWhorter et al. | 422/30 |

FOREIGN PATENT DOCUMENTS

| | | |
|---|---|---|
| EP | 0 365 501 | 4/1990 |
| GB | 791680 | 3/1958 |

OTHER PUBLICATIONS

Pfaff, John D., Method 300.1 Determination of Inorganic Anions in Drinking Water by Ion Chromatography, National Exposure Research Laboratory, Office of Research and Development, U.S. Environmental Protection Agency, Cincinnati, OH, 45268, 2007, pp. 1-40.*
Chlorine Dioxide (4500-ClO2)/Idometric Method, Inorganic NonMetals (4000), 2000, p. 4-77-4-81.*
Gordan et al. The Chemistry of Chlorine Dioxide, Progress in Inorganic Chemistry. v. 15; 1972; pp. 201-286.
Helfferich et al. Ion Exchange; 1995.
Duolite Ion—Exchange Manual; Chemical Process Company; 1960.
Gates et al. The Chlorine Dioxide Handbook, Water Disinfection Series, AWWA; 1998.
Lewatit, Bayer AG; Catalytic Removal of Dissolved Oxygen from Water.
Dence et al. Pulp Bleaching Principles and Practice. Tappi Press, 1996.
Simpson et al. A Focus of Chlorine Dioxide: The "Ideal" Biocide.
Encyclopedia. Com; Mechanism of Catalysis.
McPeak et al. Iron in Water and Processes for its Removal; 21$^{st}$ Annual Liberty Bell Corrosion Course; 1983.
Manganese Greensand CR & IR; Inversand Company; 1998.
Masschelein, Chlorine Dioxide, Chemistry and Environmental Impact of Oxychlorine Compounds; Ann Arbor Science Publishers, Inc., 1979.
XP-002227957; JP 6271301; Suido Kiko Co Ltd; 1994; abstract.
White, Handbook of Chlorination and Alternative Disinfectants; Fourth Edition; 1999, pp. 1153-1202.

* cited by examiner

*Primary Examiner* — Christine T Mui
(74) *Attorney, Agent, or Firm* — Jacobson Holman, PLLC

(57) ABSTRACT

Chlorine dioxide solutions are stabilized and prepared for storage, transportation, and testing. Each solution is separated into two samples. Chlorine dioxide is removed from one sample and then each sample is stabilized and prepared such that each sample contains only oxidized and/or reduced forms of chlorine dioxide. The stable samples may be stored, transported, and tested for chlorine dioxide. The samples are tested for the oxidized and/or reduced forms of chlorine dioxide by known methods, and mass balance equations are used to determine the concentration of chlorine dioxide in the original sample before stabilization and preparation.

30 Claims, No Drawings

METHOD OF PREPARING, STORING, TRANSPORTING AND TESTING CHLORINE DIOXIDE SOLUTIONS

CROSS-REFERENCE TO RELATED APPLICATION

This application claims priority from U.S. Provisional Patent Application No. 61/457,177, filed Jan. 21, 2011, and from U.S. Provisional Patent Application No. 61/457,094, filed Dec. 23, 2010, the disclosures of each of which are expressly incorporated herein by reference in their entirety.

FIELD OF INVENTION

The present invention relates to a method of preparing, storing, transporting, and testing chlorine dioxide solutions to determine the concentration of chlorine dioxide in those solutions. The method uses the chemistry of chlorine dioxide to modify its state such that unwanted degassing and decomposition of the test solution does not occur.

DESCRIPTION OF PRIOR ART

Chlorine dioxide is a dissolved gas in solution. It is virtually impossible to transport chlorine dioxide solutions without at least partially degassing the solution and decreasing the concentration of chlorine dioxide in the solution. In addition, chlorine dioxide is extremely sensitive to temperature, light, and concentration. In the presence of high temperature, chlorine dioxide degasses and decomposes more rapidly. In the presence of light, especially, sunlight and UV light, chlorine dioxide decomposes fairly rapidly. At high concentrations, the chlorine dioxide degasses rapidly as well as decomposes. These simple facts mean that in order for chlorine dioxide solutions to be used efficiently (they are typically used as disinfectants and oxidizers), and at maximum concentrations, the chlorine dioxide solution must be generated at or near the location where it needs to be used. As such, there are many chlorine dioxide generators used in industry.

When chlorine dioxide solutions are used for disinfection or oxidation, it is desirable to be able to determine the concentration of the chlorine dioxide in the solution at the time of, or just before, its use. This information can be used to adjust the rate at which chlorine dioxide is generated to produce the solution, and also may be required by government regulation. Therefore, it is common to take samples of the solution just prior to its use in order to test for the concentration of chlorine dioxide in the solution being used.

When testing samples of the chlorine dioxide solution for the concentration of chlorine dioxide, the foregoing properties of chlorine dioxide are still a concern. It is still a dissolved gas in solution, and will degas and/or decompose. In fact, merely transporting chlorine dioxide sample solutions over short distances within the same facility for testing can lead to gross inaccuracies of the test results, and transporting such solutions to remote sites for testing is impossible. To minimize the effects of degassing and decomposition, tests are performed as close to the point of sampling as possible, and as soon as possible after the sample is taken. In addition, many online tests (i.e. tests that measure the concentration of chlorine dioxide directly in the process stream) have been developed, but these have experienced limited commercial success. Typically online tests are used to monitor chlorine dioxide concentration for reference only, and are not typically used to control generator output.

All of these tests, whether batch or continuous, are susceptible to other contaminants in the water such as particulate matter, organic matter, and other chemicals, including chlorite ions. Some contaminants, like particulate matter or organic matter, may cause fouling of the test sensors, making the test results inaccurate. Other contaminants, like the chlorite ion, chemically interfere with the test itself, and therefore produce an inaccurate result. To prevent such interference, special membranes can be incorporated into the sensors which allow chlorine dioxide to pass through but not the chlorite ion. However, while the sensors are somewhat effective in determining the relative concentrations of chlorine dioxide and to detect trends in concentration, their lack of reliability over long periods of time makes them less effective in determining the actual concentration of the chlorine dioxide in the solution.

Moreover, it is common to want to test for the concentration of both chlorine dioxide and the chlorite ion present in the solution with the chlorine dioxide. In order to test for the concentration of chlorite ion, a gas that will not react with the contents of the solution is bubbled through the solution. The gas forces the chlorine dioxide gas out of solution, leaving a degassed solution containing chlorite ion and no chlorine dioxide. This allows for accurate measurement of the initial concentration of chlorite ions. Methods and means for degassing a solution containing chlorine dioxide are well known to those schooled in the art. Usually the process is performed by bubbling nitrogen gas or air through the solution, but any gas that does not react with the contents of the solution can be used.

It is also advantageous to be able to store or transport chlorine dioxide solutions. However, during storage or transport of chlorine dioxide solutions, chlorine dioxide can degas and release into the air causing either a potential hazard from chlorine dioxide exposure and/or a degradation of the chlorine dioxide concentration in the solution. In addition, natural decomposition of the solution occurs over time, reducing the concentration of chlorine dioxide in the stored or transported solution. Furthermore, if the solution contacts heat, light, or is agitated during storage or transport, more rapid decomposition of chlorine dioxide can occur.

Given the limitations of the current technologies, there is a need for a method of preparing, storing, transporting, and testing chlorine dioxide solutions.

SUMMARY OF THE INVENTION

In accordance with the present invention, two test samples of the solution containing chlorine dioxide are removed from the solution. This can be accomplished by different means known to those in the art, such as syringes, specially designed valves, etc.

The chlorine dioxide is stripped from the solution in the first sample (Sample 1), leaving no dissolved chlorine dioxide gas in the solution. The pH of this sample may or may not be pH adjusted. In the second sample (Sample 2), the dissolved chlorine dioxide is converted to one or more other chlorine species, which are stable, by raising the pH of Sample 2 sufficiently to completely convert the chlorine dioxide to other chlorine species, or by chemically reducing or oxidizing the chlorine dioxide in Sample 2 to completely convert the chlorine dioxide to other chlorine species. The resultant chlorine species can be chlorite ion, chlorate ion, chloride ion and/or another chlorine species. In fact, Sample 2, after raising the pH or conducting the oxidation and/or reduction reaction, may contain a mixture of the foregoing chlorine species. Once the samples are prepared (i.e. by (1) degassing, and (2)

raising the pH or oxidation or reduction), they are essentially stable so that they can be stored and transported without fear of degradation of the quality of the samples. In fact, the EPA already has preservation guidelines for the transportation of the gas-sparged chlorine dioxide samples (EPA 300.1—Determination Of Inorganic Anions In Drinking Water By Ion Chromatography). This method may be employed in the present invention to both samples. The two samples can also be tested for chlorine species concentration; a comparison of the concentrations of chlorine species in the Samples 1 and 2 can be used to calculate the concentration of chlorine dioxide in the original solution.

The testing of the chlorine species in the two test samples can be performed by any standard test for the selected chlorine species. The test can either be for a single species or for two or more species. Two common methods of testing chlorine species are by ion chromatography and amperometric measurement, although the specific testing methods used on the two prepared solutions are not an essential element of the invention. However, choosing the appropriate testing method for the various chlorine species may be important, depending on what is being tested for, but those skilled in the art will be able to choose an is appropriate testing method.

Further, the preparation and method of testing the samples as described above is not limited by the purity of the original chlorine dioxide solution. The original solution can either contain only chlorine dioxide, or it may contain other species or contaminants since their presence in the test samples would remain unchanged by the sample preparation methods, although their chemical composition could change. These other species or contaminants can include chlorite ion, chlorate ion, chloride ion, other chlorine species, or any other substance which may be present, including but not limited to, water purification chemicals, naturally occurring ions, or other additives present in the aqueous solution.

The object of the present invention, therefore, is to prepare solutions containing chlorine dioxide by taking two samples, Sample 1 and Sample 2, stripping the chlorine dioxide from Sample 1, and raising the pH of Sample 2 or oxidizing or reducing the chlorine dioxide in Sample 2 such that the chlorine dioxide in Sample 2 is completely converted to other chlorine species.

It is a further object of the present invention to facilitate storage of the prepared chlorine dioxide solution samples.

It is another object of the present invention to facilitate transport of the test sample solutions—after stripping and/or converting of chlorine dioxide—to a location remote from where the sample was taken, that location being a short or long distance away.

It is still a further object of the present invention to test for the chlorine species in each of Samples 1 and 2 and correlate the concentration of the tested chlorine species in Samples 1 and 2 to chlorine dioxide in the original sample to determine the concentration of chlorine dioxide in the original sample.

In one embodiment of the present invention, two samples of a solution containing chlorine dioxide are taken. Sample 1 is degassed such that the chlorine dioxide is removed from the solution, and either the pH of sample 2 is raised such that the chlorine dioxide in solution is completely converted to other chlorine species, or the chlorine dioxide of Sample 2 is chemically reduced or oxidized to other chlorine species.

In another embodiment of the present invention, the prepared chlorine dioxide solutions are stored.

In another embodiment of the present invention, the prepared chlorine dioxide solutions are transported.

In another embodiment of the present invention, Samples 1 and 2 above are tested for chlorine species. The difference in the two is the concentration of chlorine dioxide in the original solution being tested.

DETAILED DESCRIPTION

A solution containing chlorine dioxide is identified and two samples are taken. The samples will typically be in the 1 to 1000 ml range. Sample 1 is placed in a gas stripping column and degassed for a sufficient time to strip all of the chlorine dioxide from solution. The pH of this Sample 1 may or may not be adjusted. In Sample 2, the pH may raised by common means, such as by the addition of sodium hydroxide or another high pH solution, to a point at which all of the chlorine dioxide in solution is converted to other chlorine species. The target pH of Sample 2 will be at least 9, and preferably will be greater than 12.

Alternatively, the chlorine dioxide of Sample 2 is chemically reduced or oxidized by common means, such as by the addition of sodium bisulfate, sodium thiosulfate, or heat or UV light for reduction, or ozone, hydrogen peroxide, or contact with an anode for oxidation, to a point where all of the chlorine dioxide in solution is converted to other chlorine species. The choice of reducing agent or oxidizing agent is within the knowledge of those skilled in the art. When chemically reducing or oxidizing chlorine dioxide, other species in solution may also be reduced or oxidized. The chemical reduction or oxidation of other species does not interfere with the method of the invention, because the total chlorine species in Samples 1 and 2 are compared to determine chlorine dioxide in the original solution.

Once both Sample 1 and Sample 2 are prepared (i.e. degassed and/or had the pH raised and/or been oxidized or reduced), they may be stored and/or transported to a remote testing site, which may be in close proximity to or far from the sampling site (such as a contract testing laboratory). At the remote testing site, the appropriate testing method for the chlorine species is chosen. For example, if there is no desire to test the prepared samples for chloride ion, but there is a desire to test for chlorite ion, amperometric testing may be chosen. However, if it is determined that there is a desire to test the prepared samples for chloride ion as well as chlorite ion, ion chromatography may be chosen. Other tests which could be used include colorimetric, titrametric, and ion selective electrodes. The foregoing tests are provided merely as examples. The selection of the proper testing method and protocol is within the knowledge of those skilled in the art.

Once the appropriate testing method is chosen, both samples are tested for the chlorine species. Further buffering of the samples, either to raise or lower the pH of the samples to fit within the chosen testing protocol, may or may not be undertaken. The results of the testing are then equated to chlorine dioxide by taking the ratio of molecular weights of the chlorine species to the molecular weight of chlorine dioxide or by another method deemed appropriate by the testing method or tester. Once all chlorine species are equated to chlorine dioxide, the total amount of equivalent chlorine dioxide in Sample 1 is subtracted from the equivalent amount of chlorine dioxide in Sample 2 to obtain the concentration of chlorine dioxide in the original solution.

Hypothetical Examples

The following examples are merely hypothetical and are provided for purposes of illustration only:

Hypothetical Example 1

Two samples are taken from a solution containing chlorine dioxide.

Sample 1 is stripped with nitrogen gas and tested using ion chromatography. The sample contains 5 mg/l chlorite ion and 5 mg/l chlorate ion.

The pH of sample 2 is adjusted to 12 with NaOH and tested using ion chromotography. Since the conditions for this example are under alkaline conditions, chloride ion concentration is not measured. The sample contains 10 mg/l chlorite ion and 5 mg/l chlorate ion.

The molecular weight of chlorite ion is 67.45. The molecular weight of chlorate ion is 83.45. The molecular weight of chlorine dioxide is 67.45.

Sample 1 contains the following concentrations of ions, expressed as chlorine dioxide:
5 mg/l chlorite ion=5 mg/l as chlorine dioxide
5 mg/l chlorate ion=4.04 mg/l as chlorine dioxide Sample 2 contains the following concentrations of ions, expressed as chlorine dioxide:
10 mg/l chlorite ion=10 mg/l as chlorine dioxide
5 mg/l chlorate ion=4.04 mg/l as chlorine dioxide Subtracting the results of sample 1 from sample 2 yields the following:

Sample 2 (10+4.04)−Sample 1 (5+4.04)=5 mg/l of chlorine dioxide in the original solution.

Hypothetical Example 2

Two samples are taken from a solution containing chlorine dioxide.

Sample 1 is stripped with nitrogen gas and tested using ion chromatography. The sample contains 5 mg/l chlorite ion, 5 mg/l chlorate ion, and 10 mg/l chloride ion.

The chlorine dioxide in sample 2 is chemically reduced with sodium thiosulfate and tested using ion chromatography. The sample contains 0 mg/l chlorite ion, 0 mg/l chlorate ion, and 200 mg/l chloride ion.

The molecular weight of chlorite ion is 67.45. The molecular weight of chlorate ion is 83.45. The molecular weight of chloride ion is 35.45. The molecular weight of chlorine dioxide is 67.45.

Sample 1 contains the following concentrations of ions, expressed as chlorine dioxide:
5 mg/l chlorite ion=5 mg/l as chlorine dioxide
5 mg/l chlorate ion=4.04 mg/l as chlorine dioxide
10 mg/l chloride ion=19.03 mg/l as chlorine dioxide Sample 2 contains the following concentrations of ions, expressed as chlorine dioxide:
0 mg/l chlorite ion=0 mg/l as chlorine dioxide
0 mg/l chlorate ion=0 mg/l as chlorine dioxide
200 mg/l chloride ion=380.54 mg/l as chlorine dioxide Subtracting the results of sample 1 from sample 2 yields the following.

Sample 2 (0+0+380.54)−Sample 1 (5+4.04+19.03)=352.47 mg/l of chlorine dioxide in the original solution.

Hypothetical Example 3

Two samples are taken from a solution containing chlorine dioxide.

Sample 1 is stripped with nitrogen gas and tested using ion chromatography. The sample contains 5 mg/l chlorite ion, 5 mg/l chlorate ion, and 10 mg/l chloride ion.

The chlorine dioxide in sample 2 is chemically oxidized with ozone and tested using ion chromatography. The sample contains 0 mg/l chlorite ion, 100 mg/l chlorate ion, and 0 mg/l chloride ion.

The molecular weight of chlorite ion is 67.45. The molecular weight of chlorate ion is 83.45. The molecular weight of chloride ion is 35.45. The molecular weight of chlorine dioxide is 67.45.

Sample 1 contains the following concentrations of ions, expressed as chlorine dioxide:
5 mg/l chlorite ion=5 mg/l as chlorine dioxide
5 mg/l chlorate ion=4.04 mg/l as chlorine dioxide
10 mg/l chloride ion=19.03 mg/l as chlorine dioxide Sample 2 contains the following concentrations of ions, expressed as chlorine dioxide.
0 mg/l chlorite ion=0 mg/l as chlorine dioxide
100 mg/l chlorate ion=80.83 mg/l as chlorine dioxide
0 mg/l chloride ion=0 mg/l as chlorine dioxide Subtracting the results of sample 1 from sample 2 yields the following:

Sample 2 (0+80.83+0)−Sample 1 (5+4.04+19.03)=52.76 mg/l of chlorine dioxide in the original solution.

Actual Example

Chlorine dioxide, chlorite, and chlorate concentrations were tested using EPA method 300.1 "Determination of Inorganic Anions by Ion Chromatography," Part B following a particular sample preparation procedure as described in the present invention. A Dionex DX 500 Ion Chromatograph (IC) was used. The IC was calibrated using a blank and six standards ranging from 0.1 to 20 ppm chlorate and chlorite. The method detection limits for chlorite and chlorate were determined to be 0.015 ppm and 0.022 ppm, respectively. Samples were diluted so that analytes were within the calibration range.

Each sample was analyzed sparged and unsparged. Approximately 100-200 uL of 5 N soldium hydroxide was added to 10-15 mL of the unsparged sample aliquots to bring the pH to 12+/−0.05. A minimum of one hour after the pH adjustment, the samples were analyzed by IC. The sparged fraction was purged with nitrogen gas for 15 minutes, and the pH was adjusted with the 5 N sodium hydroxide to bring the pH to 12+/−0.5.

Chlorite and chlorate are by-products of chlorine dioxide under alkaline conditions, according to the following reaction:

$$2ClO_2 + 2OH^- \rightarrow ClO_2^- + ClO_3^- + H_2O$$

Because the conditions in this example are alkaline, chloride concentration is not measured.

However, the mole ratios of the by-products are thought to be disproportionate and dependent on the conditions (pH, time, temperature, UV light). The chlorite and chlorate found in the sparged sample represents the chlorite and chlorate found in the original sample. The chlorite and chlorate found in the non-sparged sample represents the chlorine dioxide plus the chlorite and chlorate in the original sample. The differences represent the chlorine dioxide concentration of the original sample.

Calculations for chlorite and chlorine dioxide for the modified EPA method 300.1, Part B Ion Chromatography method

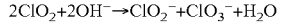

Chlorite, mg $ClO_2^-/L = C_{chlorite\ NS}$

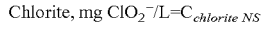

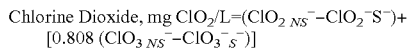

Chlorine Dioxide, mg $ClO_2/L = (ClO_{2\ NS}^- - ClO_2^- S^-) + [0.808\ (ClO_{3\ NS}^- - ClO_{3\ S}^-)]$ where:
$ClO_2^-{}_{NS}$=Chlorite concentration in non-sparged sample, mg/L
$ClO_3^-{}_{NS}$=Chlorate concentration in non-sparged sample, mg/L
$ClO_2^-{}_S$=Chlorite concentration in sparged sample, mg/L
$ClO_3^-{}_S$=Chlorate concentration in sparged sample, mg/L
0.808=(67.5/83.5)=molecular weight ratio of chlorite to chlorate The same samples were also run using Standard Method 4500-ClO$_2$ E. Amperometric Method II for comparison purposes. A Mettler Toledo G20 Compact Titrator was used for the analysis. The results of the testing are shown in Table 1 below.

TABLE 1

| Sample Dilution | Chlorine Dioxide | | Chlorite | | Chlorate IC, ppm, stabilized sample |
|---|---|---|---|---|---|
| | Amperometric Titration, ppm | IC, ppm, stabilized sample | Amperometric Titration, ppm | IC, ppm, stabilized sample | |
| none | 530 | 499 | 65.6 | 58.3 | 59.4 |
| 1:1 | 259 | 252 | 27 | 28.4 | 38.7 |
| 1:100 | 4.92 | 4.48 | 0.67 | 0.664 | 0.76 |
| 1:1000 | 0.418 | 0.423 | 0.134 | 0.126 | 0.08 |

Although IC was used to test the modified sample, Amperometric Titration or any other test method could have also been used in the present invention. For this particular example, IC was chosen to test the prepared sample, because it is the EPA approved method for testing both chlorite and chlorate, whereas Amperometric Titration is only approved to test for chlorite and chlorine dioxide. It was not necessary to test for chlorine dioxide in the prepared sample, because the concentration of chlorine dioxide is determined from the testing of chlorite and chlorate, so the IC method is appropriate. In practice, the IC method is much easier and faster to use than Amperometric Titration.

The foregoing descriptions should be considered as illustrative only of the principles of the invention. Since numerous applications of the present invention will readily occur to those skilled in the art, it is not desired to limit the invention to the exact method described. Rather, all suitable modifications and equivalents may be resorted to, falling within the scope of the invention.

What is claimed is:

1. A method for preparing and stabilizing chlorine dioxide samples for transport, storage, or testing, which comprises taking at least two samples, Sample 1 and Sample 2, from a chlorine dioxide solution to be tested, the samples then being processed as follows:
   stripping the chlorine dioxide from Sample 1, and
   raising the pH of Sample 2 so as to completely convert the chlorine dioxide in solution to other stable chlorine species.

2. The method of claim 1, wherein the chlorine dioxide is stripped from Sample 1 using nitrogen gas.

3. The method of claim 1, wherein the pH of Sample 2 is raised above 9.

4. The method of claim 1, wherein the pH of Sample 2 is raised above 12.

5. The method of claim 1, wherein the prepared samples are stored.

6. The method of claim 1, wherein the prepared samples are transported.

7. The method of claim 6, wherein the prepared samples are transported to an outside facility for testing.

8. The method of claim 1 wherein the prepared samples are tested for some or all chlorine species.

9. The method of claim 8 wherein the test results are correlated to chlorine dioxide, the results of Sample 1 are subtracted from the results of Sample 2, and the concentration of chlorine dioxide in the solution that was originally sampled is determined.

10. A method for determining the concentration of chlorine dioxide in a chlorine dioxide solution in a facility comprising the following steps:
   (1) isolating two samples, Sample 1 and Sample 2, from the chlorine dioxide solution;
   (2) treating Sample 1 by stripping the chlorine dioxide from it;
   (3) treating Sample 2 by raising its pH sufficiently so as to completely convert the chlorine dioxide in solution to other stable chlorine species;
   (4) transporting the treated Samples 1 and 2 to a testing site;
   (5) testing Samples 1 and 3 for the contraction of chlorine-containing species therein; and
   (6) using the information obtained in step (5) to calculate the concentration of chlorine dioxide in the chlorine dioxide solution.

11. The method of claim 10, wherein Samples 1 and 2 are transported within the same facility for testing.

12. The method of claim 10, wherein Samples 1 and 2 are transported to a different facility for testing.

13. The method of claim 10, wherein Samples 1 and 2 are stored after before treated in steps (2) and (3) and before being tested in step (5).

14. A method for preparing chlorine dioxide samples for transport, storage, or testing, such that at least two samples, Sample 1 and Sample 2 are taken, and the samples are processed as follows:
   stripping the chlorine dioxide from Sample 1, and chemically reducing or oxidizing the chlorine dioxide of sample 2 so as to completely convert the chlorine dioxide in solution to other stable chlorine species.

15. The method of claim 14, wherein the chlorine dioxide is stripped from Sample 1 using nitrogen, helium, or other inert gas.

16. The method of claim 14, wherein Sample 2 is chemically reduced using sodium bisulfate.

17. The method of claim 14, wherein Sample 2 is chemically reduced using sodium thiosulfate.

18. The method of claim 14, wherein Sample 2 is chemically reduced using heat.

19. The method of claim 14, wherein Sample 2 is chemically reduced using UV light.

20. The method of claim 14, wherein Sample 2 is chemically oxidized using ozone.

21. The method of claim 14, wherein Sample 2 is chemically oxidized using hydrogen peroxide.

22. The method of claim 14, wherein Sample 2 is oxidized such that the oxidation occurs electrochemically in the presence of an anode.

23. The method of claim 14, wherein the prepared samples are stored.

24. The method of claim 14, wherein the prepared samples are transported.

25. The method of claim 14 wherein the prepared samples are transported to an outside facility for testing.

26. The method of claim 14 wherein each of Samples 1 and 2 are tested for some or all chlorine species.

27. The method of claim 21 wherein the test results are correlated to chlorine dioxide, the results or Sample 1 are subtracted from the results of Sample 2, and the concentration of chlorine dioxide in the solution that was originally sampled is determined.

28. A method for determining the concentration of chlorine dioxide in a chlorine dioxide solution comprising the following steps:
 (1) isolating two samples, Sample 1 and Sample 2, from the chlorine dioxide solution;
 (2) stripping the chlorine dioxide from Sample 1;
 (3) completely converting the chlorine dioxide in Sample 2 to other stable chlorine species;
 (4) separately determining the concentration of the chlorine containing species in each of Samples 1 and 2; and
 (5) calculating the concentration of chlorine dioxide in said chlorine dioxide solution based upon the information obtained in step (4).

29. The method of claim 28 wherein the complete conversion of the chlorine dioxide in Sample 2 is accomplished by sufficiently raising the pH, chemically reducing the chlorine dioxide or chemically oxidizing the chlorine dioxide, of Sample 2, so as to completely convert the chlorine dioxide in solution to other chlorine species.

30. The method of claim 28, wherein the samples are transported to a remote location between steps (3) and (4).

* * * * *